United States Patent [19]

Thompson et al.

[11] Patent Number: 5,610,052
[45] Date of Patent: Mar. 11, 1997

[54] ENZYMATIC RNA WITH ACTIVITY TO RAS

[75] Inventors: James D. Thompson; Kenneth G. Draper, both of Boulder, Colo.

[73] Assignee: Ribozyme Pharmaceuticals Inc., Boulder, Colo.

[21] Appl. No.: 936,110

[22] Filed: Aug. 26, 1992

[51] Int. Cl.⁶ .............................. C12N 5/00; C07H 21/04
[52] U.S. Cl. ..................... 435/366; 536/23.2; 536/24.5; 435/363
[58] Field of Search .......................... 514/44; 435/320.1, 435/199, 172.3, 240.1; 935/44, 46; 536/23.2

[56] References Cited

FOREIGN PATENT DOCUMENTS

| | | |
|---|---|---|
| 9115580 | 10/1991 | WIPO . |
| 9118624 | 12/1991 | WIPO . |
| 9118625 | 12/1991 | WIPO . |
| 9118913 | 12/1991 | WIPO . |
| 9200080 | 1/1992 | WIPO . |

OTHER PUBLICATIONS

Hampel et al., "RNA Catalyst for Cleaving Specific RNA Sequences", filed Sep. 20, 1989, which is a Continuation-in-Part of U.S. Serial No. 07/247,100 filed Sep. 20, 1988.
Perrotta and Been, 31 *Biochemistry* 16, 1992.
Hampel and Tritz, 28 *Biochemistry* 4929, 1989.
Hampel et al., 18 *Nucleic Acids Research* 299, 1990.
Weerasinghe et al., 65 *Journal of Virology* 5531, 1991.
Mamone et al., "Design of Hammerhead Ribozymes Targeted to Sequences in HIV, HSV, and the RAT ANF GENE", Abstract of Keystone, CO (May 27, 1992).
Pavco et al., "Regulation of Self-Splicing Reactions by Antisense RNA", Abstract of Keystone, CO (May 27, 1992).
Haseloff and Gerlach, 334 *Nature* 585, 1988.
Guerrier-Takada et al., 35 *Cell* 849, 1983.
Tseng et al (1994) Cancer Gene Therapy 1, 65–71.
"Oncogenes: An Introduction to the Concept of Cancer Genes", Burck et al, Springer-Verlag, New York 1988, pp. 182–197.
"Oncogenes", G. M. Copper, Jones–Bartlett Publishers, Boston 1990, pp. 141–159.
"Harrison's Principles of Internal Medicine", vol. I. Isselbacher et al eds, 1994, pp. 374–380 and pp. 1116–1331.
Sarver et al (1990) Science 247, 1222–1225.
McGrath et al (1983) Nature 304, 501–506.

*Primary Examiner*—Jacqueline M. Stone
*Assistant Examiner*—Deborah Crouch
*Attorney, Agent, or Firm*—Lyon & Lyon

[57] ABSTRACT

An enzymatic RNA molecule which cleaves mRNA associated with development or maintenance of colon carcinoma.

12 Claims, 1 Drawing Sheet

ENZYMATIC RNA WITH ACTIVITY TO RAS

BACKGROUND OF THE INVENTION

This invention relates to methods for inhibition of growth of transformed cells, and inhibition of progression to a transformed phenotype in pre-neoplastic cells.

Transformation is a cumulative process whereby normal control of cell growth and differentiation is interrupted, usually through the accumulation of mutations affecting the expression of genes that regulate cell growth and differentiation.

Scanlon WO91/18625, WO91/18624, and WO91/18913 describes a ribozyme effective to cleave oncogene RNA from the H-ras gene. This ribozyme is said to inhibit H-ras expression in response to exogenous stimuli. Reddy WO92/00080 describes use of ribozymes as therapeutic agents for leukemias, such as CML by targeting specific portions of the BCR-ABL gene transcript.

The platelet derived growth factor (PDGF) system has served as a prototype for identification of substrates of the receptor tyrosine kinases. Certain enzymes become activated by the PDGF receptor kinase, including phospholipase C and phosphatidylinositol 3' kinase, Ras guanosine triphosphate (GTPase) activating protein (GAP) and src-like tyrosine kinases. GAP regulates the function of the Ras protein. It stimulates the GTPase activity of the 21 kD Ras protein. Barbacid. 56 *Ann. Rev. Biochem.* 779, 1987. Microinjection of oncogenically activated Ras into NIH 3T3 cells induces DNA synthesis. Mutations that cause oncogenic activation of ras lead to accumulation of Ras bound to GTP, the active form of the molecule. These mutations block the ability of GAP to convert Ras to the inactive form. Mutations that impair the interactions of Ras with GAP also block the biological function of Ras.

While a number of ras alleles exist (N-ras, K-ras, H-ras) which have been implicated in carcinogenesis, the type most often associated with colon and pancreatic carcinomas is the K-ras. Ribozymes which are targeted to certain regions of the K-ras allelic mRNAs may also prove inhibitory to the function of the other allelic mRNAs of the N-ras and H-ras genes.

SUMMARY OF THE INVENTION

The invention features use of ribozymes to inhibit the development or expression of a transformed phenotype in man and other animals by modulating expression of a gene that contributes to the expression of colon carcinoma. Cleavage of targeted mRNAs expressed in pre-neoplastic and transformed cells elicits inhibition of the transformed state.

Ribozymes are RNA molecules having an enzymatic activity which is able to repeatedly cleave other separate RNA molecules in a nucleotide base sequence specific manner. Such enzymatic RNA molecules can be targeted to virtually any RNA transcript and efficient cleavage has been achieved in vitro. Kim et al., 84 *Proc. Natl. Acad. of Sci. USA* 8788, 1987, Haseloff and Gerlach, 334 *Nature* 585, 1988, Cech, 260 *JAMA* 3030, 1988, and Jefferies et al., 17 *Nucleic Acid Research* 1371, 1989.

Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

This class of chemicals exhibits a high degree of specificity for cleavage of the intended target mRNA. Consequently, the ribozyme agent will only affect cells expressing that particular gene, and will not be toxic to normal tissues.

The invention can be used to treat cancer or pre-neoplastic conditions. Two preferred administration protocols can be used, either in vivo administration to reduce the tumor burden, or ex vivo treatment to eradicate transformed cells from tissues such as bone marrow prior to reimplantation.

Thus, in the first aspect the invention features an enzymatic RNA molecule (or ribozyme) which cleaves mRNA associated with development or maintenance of colon carcinoma, e.g., those mRNAs produced from the gene K-ras, including mRNA targets disclosed in Table 1.

TABLE 1

| Nucleotide | Target mRNA sequence | ID. NOS. |
|---|---|---|
| (1) | UCCUAGGCGGCG | SEQ. ID. NO. 1 |
| (18) | GGCGGCGGAGGCAGCAGCG | SEQ. ID. NO. 2 |
| (42) | GGCAGUGGCGGCGG | SEQ. ID. NO. 3 |
| (68) | CGGCUCGGCCAGUACUCCCGGCCC | SEQ. ID. NO. 4 |
| (120) | GCGCAGGCACUGAAGGCGGCGGCGGGGCCAGAGGCUCAG | SEQ. ID. NO. 5 |
| (203) | AUAAACUUGUGGUAGUUGGAGCUUGUGGCGU | SEQ. ID. NO. 6 |
| (248) | UGACGAUACAGCUA | SEQ. ID. NO. 7 |
| (275) | UUGUGGACGAAUAUGAUCCAACAAUA | SEQ. ID. NO. 8 |

TABLE 1-continued

| Nucleotide | Target mRNA sequence | ID. NOS. |
|---|---|---|
| (307) | UCCUACAGGAAGCAAGUAGUAAUUGAU | SEQ. ID. NO. 9 |
| (374) | AAGAGGAGUACAGUGCAAUGAGGGA | SEQ. ID. NO. 10 |
| (435) | AUUUGCCAUAAAUAAUACUAAAUCAUUUGAA | SEQ. ID. NO. 11 |
| (466) | GAUAUUCACCAUUAUAGAGAACAAAUUAAA | SEQ. ID. NO. 12 |
| (511) | GAAGAUGUACCUAUGGUCCUAGUAGGAAAUAAAUGU | SEQ. ID. NO. 13 |
| (547) | GAUUUGCCUUCUAGAACAGUAG | SEQ. ID. NO. 14 |
| (602) | AUGGAAUUCCU | SEQ. ID. NO. 15 |
| (631) | AAGACAAGACAGGG | SEQ. ID. NO. 16 |
| (675) | AGAAAUUCGAA | SEQ. ID. NO. 17 |
| (686) | AACAUAAAGAAAAGAUGAGCAAAGAUGGUAAAAAGA | SEQ. ID. NO. 18 |
| (722) | AGAAAAAGAAGUCAAAGACAAAGUGUGUA | SEQ. ID. NO. 19 |
| (781) | UAAGGCAUACUAGU | SEQ. ID. NO. 20 |
| (820) | ACUAAAUUAUUAG | SEQ. ID. NO. 21 |
| (840) | UUUAGCAUUACCUAA | SEQ. ID. NO. 22 |
| (863) | CUGCUCCAUGCAGACUGUUAGC | SEQ. ID. NO. 23 |
| (907) | AAAAUGACAGUGGA | SEQ. ID. NO. 24 |
| (946) | UAUUCCCAGAGUU | SEQ. ID. NO. 25 |
| (970) | ACUAGCAAUGCCUGU | SEQ. ID. NO. 26 |

By "enzymatic RNA molecule" it is meant an RNA molecule which has complementarity in a substrate binding region to a specified mRNA target, and also has an enzymatic activity which is active to specifically cleave that mRNA. That is, the enzymatic RNA molecule is able to intermolecularly cleave mRNA and thereby inactivate a target mRNA molecule. This complementarity functions to allow sufficient hybridization of the enzymatic RNA molecule to the target RNA to allow the cleavage to occur. One hundred percent complementarity is preferred, but complementarity as low as 50–75% may also be useful in this invention.

In preferred embodiments, the enzymatic RNA molecule is formed in a hammerhead motif, but may also be formed in the motif of a hairpin, hepatitis delta virus, group I intron or RNAseP-like RNA (in association with an RNA guide sequence). Examples of such hammerhead motifs are described by Rossi et al., 8 AIDS RESEARCH AND HUMAN RETROVIRUSES 183, 1992, of hairpin motifs by Hampel et al., RNA CATALYST FOR CLEAVING SPECIFIC RNA SEQUENCES, filed Sep. 20, 1989, which is a continuation-in-part of U.S. Ser. No. 07/247,100 filed Sep. 20, 1988, Hampel and Tritz, 28 *Biochemistry* 4929, 1989 and Hampel et al., 18 *Nucleic Acids Research* 299, 1990, and an example of the hepatitis delta virus motif is described by Perrotta and Been, 31 *Biochemistry* 16, 1992, of the RNAseP motif by Guerrier-Takada, et al., 35 *Cell* 849, 1983, and of the group I intron by Cech et al., U.S. Pat. No. 4,987,071. These specific motifs are not limiting in the invention and those skilled in the art will recognize that all that is important in an enzymatic RNA molecule of this invention is that it has a specific substrate binding site which is complementary to one or more of the target gene RNA regions, and that it have nucleotide sequences within or surrounding that substrate binding site which impart an RNA cleaving activity to the molecule.

In a second related aspect, the invention features a mammalian cell which includes an enzymatic RNA molecule as described above. Preferably, the mammalian cell is a human cell.

In a third related aspect, the invention features an expression vector which includes nucleic acid encoding an enzymatic RNA molecule described above, located in the vector, e.g., in a manner which allows expression of that enzymatic RNA molecule within a mammalian cell.

In a fourth related aspect, the invention features a method for treatment of colon carcinoma by administering to a patient an enzymatic RNA molecule as described above.

The invention provides a class of chemical cleaving agents which exhibit a high degree of specificity for the mRNA causative of colon carcinoma. Such enzymatic RNA molecules can be delivered exogenously or endogenously to infected cells. In the preferred hammerhead motif the small size (less than 40 nucleotides, preferably between 32 and 36 nucleotides in length) of the molecule allows the cost of treatment to be reduced.

The smallest ribozyme delivered for any type of treatment reported to date (by Rossi et al., 1992 supra). is an in vitro transcript having a length of 142 nucleotides. Synthesis of ribozymes greater than 100 nucleotides in length is very difficult using automated methods, and the therapeutic cost of such molecules is prohibitive. Delivery of ribozymes by expression vectors is primarily feasible using only ex vivo treatments. This limits the utility of this approach. In this invention, an alternative approach uses smaller ribozyme motifs (e.g., of the hammerhead structure, shown generally in FIG. 1) and exogenous delivery. The simple structure of these molecules also increases the ability of the ribozyme to invade targeted regions of the mRNA structure. Thus, unlike the situation when the hammerhead structure is included within longer transcripts, there are no non-ribozyme flanking sequences to interfere with correct folding of the ribozyme structure, as well as complementary binding of the ribozyme to the mRNA target.

The enzymatic RNA molecules of this invention can be used to treat human colon carcinoma or precancerous conditions. Such treatment can also be extended to other related genes in nonhuman primates. Affected animals can be treated at the time of cancer detection or in a prophylactic manner. This timing of treatment will reduce the number of affected cells and disable cellular replication. This is possible because the ribozymes are designed to disable structures required for successful cellular proliferation.

Other features and advantages of the invention will be apparent from the following description of the preferred embodiments thereof, and from the claims.

DESCRIPTION OF THE PREFERRED EMBODIMENTS

Figure 1:
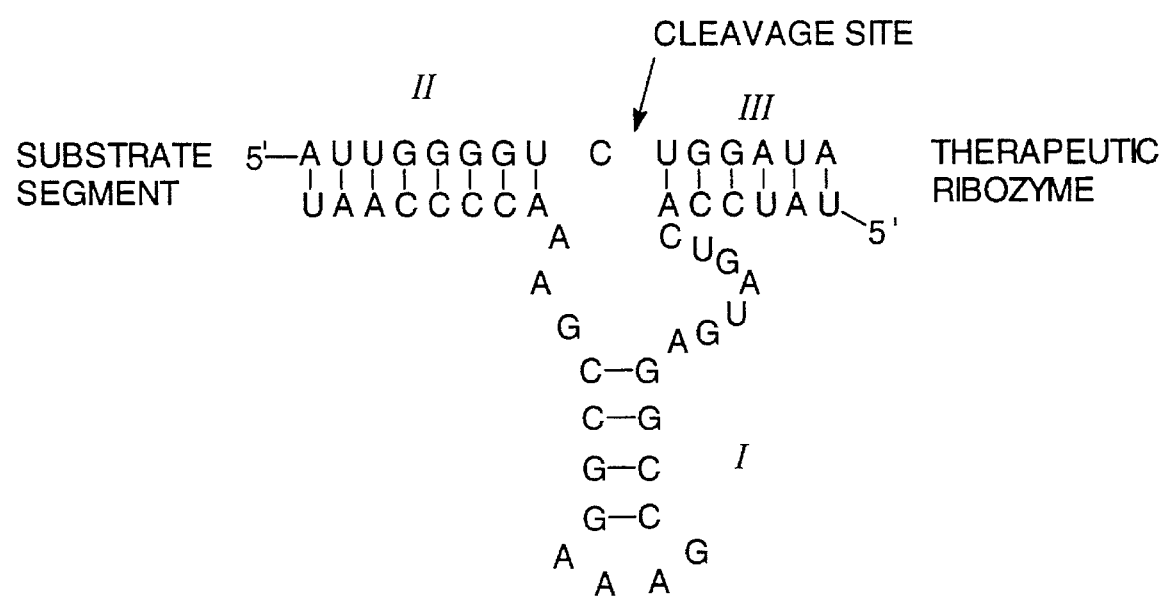

The drawing will first briefly be described.

DRAWING

FIG. 1 is a diagrammatic representation of a hammerhead motif ribozyme showing stems I, II and III (marked (I), (II) and (III) respectively) interacting with a viral target region. The 5' and 3' ends of both ribozyme and target are shown. Dashes indicate base-paired nucleotides.

TARGET SITES

Ribozymes targeting selected regions of mRNA associated with tumor cell growth are chosen to cleave the target RNA in a manner which preferably inhibits translation of the RNA. Genes are selected such that inhibition of translation will preferably inhibit cell replication, e.g., by inhibiting production of a necessary protein. Selection of effective target sites within these critical regions of mRNA entails testing the accessibility of the target RNA to hybridization with various oligonucleotide probes. These studies can be performed using RNA probes and assaying accessibility by cleaving the hybrid molecule with RNAseH (see below). Alternatively, such a study can use ribozyme probes designed from secondary structure predictions of the mRNAs, and assaying cleavage products by polyacrylamide gel electrophoresis (PAGE), to detect the presence of cleaved and uncleaved molecules.

The following is but one example of a method by which suitable target sites can be identified and is not limiting in this invention. Generally, the method involves identifying potential cleavage sites for a hammerhead ribozyme, and then testing each of these sites to determine their suitability as targets by ensuring that secondary structure formation is minimal.

The mRNA sequences are compared in an appropriate target region. Putative ribozyme cleavage sites are found. These sites represent the preferable sites for hammerhead ribozyme cleavage within these two target mRNAs.

Short RNA substrates corresponding to each of the mRNA sites are designed. Each substrate is composed of two to three nucleotides at the 5' and 3' ends that will not base pair with a corresponding ribozyme recognition region. The unpaired regions flanked a central region of 12–14 nucleotides to which complementary arms in the ribozyme are designed.

The structure of each substrate sequence is predicted using a PC fold computer program. Sequences which give a positive free energy of binding are accepted. Sequences which give a negative free energy are modified by trimming one or two bases from each of the ends. If the modified sequences are still predicted to have a strong secondary structure, they are rejected.

After substrates are chosen, ribozymes are designed to each of the RNA substrates. Ribozyme folding is also analyzed using PC fold.

Ribozyme molecules are sought which form hammerhead motif stem II (see FIG. 1) regions and contain flanking arms which are devoid of intramolecular base pairing. Often the ribozymes are modified by trimming a base from the ends of the ribozyme, or by introducing additional base pairs in stem II to achieve the desired fold. Ribozymes with incorrect folding are rejected. After substrate/ribozyme pairs are found to contain correct intramolecular structures, the molecules are folded together to predict intermolecular interactions. A schematic representation of a ribozyme with its coordinate base pairing to its cognate target sequence is shown in FIG. 1. Examples of useful targets are listed above in Table 1.

Those targets thought to be useful as ribozyme targets can be tested to determine accessibility to nucleic acid probes in a ribonuclease H assay (see below). This assay provides a quick test of the use of the target site without requiring synthesis of a ribozyme. It can be used to screen for sites most suited for ribozyme attack.

Synthesis of Ribozymes

Ribozymes useful in this invention can be produced by gene transcription as described by Cech, supra, or by chemical synthesis. Chemical synthesis of RNA is similar to that for DNA synthesis. The additional 2'—OH group in RNA, however, requires a different protecting group strategy to deal with selective 3'–5' internucleotide bond formation, and with RNA susceptibility to degradation in the presence of bases. The recently developed method of RNA synthesis utilizing the t-butyldimethylsilyl group for the protection of the 2' hydroxyl is the most reliable method for synthesis of ribozymes. The method reproducibly yields RNA with the correct 3'–5' internucleotide linkages, with average coupling yields in excess of 99%, and requires only a two-step deprotection of the polymer.

A method, based upon H-phosphonate chemistry of phosphoroamidites gives a relatively lower coupling efficiency than a method based upon phosphoroamidite chemistry. This is a problem for synthesis of DNA as well. A promising approach to scale-up of automatic oligonucleotide synthesis has been described recently for the H-phosphonates. A combination of a proper coupling time and additional capping of "failure" sequences gave high yields in the synthesis of oligodeoxynucleotides in scales in the range of 14 μmoles with as little as 2 equivalents of a monomer in the coupling step. Another alternative approach is to use soluble polymeric supports (e.g., polyethylene glycols), instead of the conventional solid supports. This method can yield short oligonucleotides in hundred milligram quantities per batch utilizing about 3 equivalents of a monomer in a coupling step.

Various modifications to ribozyme structure can be made to enhance the utility of ribozymes. Such modifications will enhance shelf-life, half-life in vitro, stability, and ease of introduction of such ribozymes to the target site, e.g., to enhance penetration of cellular membranes, and confer the ability to recognize and bind to targeted cells.

Exogenous delivery of ribozymes benefits from chemical modification of the backbone, e.g., by the overall negative charge of the ribozyme molecule being reduced to facilitate diffusion across the cell membrane. The present strategies for reducing the oligonucleotide charge include: modification of internucleotide linkages by methylphosphonates, use of phosphoramidites, linking oligonucleotides to positively charged molecules, and creating complex packages composed of oligonucleotides, lipids and specific receptors or effectors for targeted cells. Examples of such modifications include sulfur-containing ribozymes containing phosphorothioates and phosphorodithioates as internucleotide linkages in RNA. Synthesis of such sulfur-modified ribozymes is achieved by use of the sulfur-transfer reagent, $^3$H-1,2-benzenedithiol-3-one 1,1-dioxide. Ribozymes may also contain ribose modified ribonucleotides. Pyrimidine analogues are prepared from uridine using a procedure employing diethylamino sulphur trifluoride (DAST) as a starting reagent. Ribozymes can also be either electrostatically or covalently attached to polymeric cations for the purpose of reducing charge. The polymer can be attached to the ribozyme by simply converting the 3'-end to a ribonucleoside dialdehyde which is obtained by a periodate cleavage of the terminal 2',3'-cis diol system. Depending on the specific requirements for delivery systems, other possible modifications may include different linker arms containing carboxyl, amino or thiol functionalities. Yet further examples include use of methylphosphonates and 2'-o-methylribose and 5' or 3' capping or blocking with $m_7GpppG$ or $m_3^{2,2,7}GpppG$.

For example, a kinased ribozyme is contacted with guanosine triphosphate and guanyltransferase to add a $m^3G$ cap to the ribozyme. After such synthesis, the ribozyme can be gel purified using standard procedure. To ensure that the ribozyme has the desired activity, it may be tested with and without the 5' cap using standard procedures to assay both its enzymatic activity and its stability.

Synthetic ribozymes, including those containing various modifiers, can be purified by high pressure liquid chromatography (HPLC). Other liquid chromatography techniques, employing reverse phase columns and anion exchangers on silica and polymeric supports may also be used.

There follows an example of the synthesis of one ribozyme. (See Dudycz, U.S. Ser. No. 07/884,436, filed May 14, 1992, hereby incorporated by reference herein.) A solid phase phosphoramidite chemistry was employed. Monomers used were 2'-tert-butyl-dimethylsilyl cyanoethylphosphoramidities of uridine, N-benzoyl-cytosine, N-phenoxyacetyl adenosine and guanosine (Glen Research, Sterling, Va.). Solid phase synthesis was carried out on either an ABI 394 or 380B DNA/RNA synthesizer using the standard protocol provided with each machine. The only exception was that the coupling step was increased from 10 to 12 minutes. The phosphoramidite concentration was 0.1 M. Synthesis was done on a 1 μmole scale using a 1 μmole RNA reaction column (Glen Research). The average coupling efficiencies were between 97% and 98% for the 394 model, and between 97% and 99% for the 380B model, as determined by a calorimetric measurement of the released trityl cation.

Blocked ribozymes were cleaved from the solid support (e.g., CPG), and the bases and diphosphoester moiety deprotected in a sterile vial by dry ethanolic ammonia (2 mL) at 55° C. for 16 hours. The reaction mixture was cooled on dry ice. Later, the cold liquid was transferred into a sterile screw cap vial and lyophilized.

To remove the 2'-tert-butyl-dimethylsilyl groups from the ribozyme, the residue was suspended in 1M tetra-n-butylammonium fluoride in dry THF (TBAF), using a 20 fold excess of the reagent for every silyl group, for 16 hours at ambient temperature (about 15°–25° C.). The reaction was quenched by adding an equal volume of sterile 1M triethylamine acetate, pH 6.5. The sample was cooled and concentrated on a SpeedVac to the half of the initial volume.

The ribozymes were purified in two steps by HPLC on a C4 300 Å 5 mmDeltaPak column in an acetonitrile gradient.

The first step, or "trityl on" step, was a separation of 5'-DMT-protected ribozyme(s) from failure sequences lacking a 5'-DMT group. Solvents used for this step were: A (0.1M triethylammoniumacetate, pH 6.8) and B (acetonitrile). The elution profile was: 20% B for 10 minutes, followed by a linear gradient of 20% B to 50% B over 50 minutes, 50% B for 10 minutes, a linear gradient of 50% B to 100% B over 10 minutes, and a linear gradient of 100% B to 0% B over 10 minutes.

The second step was a purification of a completely deblocked ribozyme by a treatment of 2% trifluoroacetic acid on a C4 300 Å 5 mmDeltaPak column in an acetonitrile gradient. Solvents used for this second step were: A (0.1M Triethylammoniumacetate, pH 6.8) and B (80% acetonitrile, 0.1M triethylammonium acetate, pH 6.8). The elution profile was: 5% B for 5 minutes, a linear gradient of 5% B to 15% B over 60 minutes, 15% B for 10 minutes, and a linear gradient of 15% B to 0% B over 10 minutes.

The fraction containing ribozyme was cooled and lyophilized on a SpeedVac. Solid residue was dissolved in a minimum amount of ethanol and sodium perchlorate in acetone. The ribozyme was collected by centrifugation, washed three times with acetone, and lyophilized.

Expression Vector

While synthetic ribozymes are preferred in this invention, those produced by expression vectors can also be used. (See McSwiggen, U.S. Ser. No. 07/884,431, filed May 14, 1992, hereby incorporated by reference herein.) In designing a suitable ribozyme expression vector the following factors are important to consider. The final ribozyme must be kept as small as possible to minimize unwanted secondary structure within the ribozyme. A promoter (e.g., a human cytomegalovirus immediate early promoter or the U6 snRNA promoter) should be chosen to be a relatively strong promoter, and expressible both in vitro and in vivo (e.g., the human cytomegalovirus promoter or the human beta actin promoter). Such a promoter should express the ribozyme at a level suitable to effect production of enough ribozyme to destroy a target RNA, but not at too high a level to prevent other cellular activities from occurring (unless cell death itself is desired).

A hairpin at the 5' end of the ribozyme is useful to ensure that the required transcription initiation sequence (GG or GGG or GGGAG) does not bind to some other part of the ribozyme and thus affect regulation of the transcription process. The 5' hairpin is also useful to protect the ribozyme from 5'-3' exonucleases. A selected hairpin at the 3' end of the ribozyme gene is useful since it acts as a transcription termination signal, and protects the ribozyme from 3'-5' exonuclease activity. One example of a known termination signal is that present on the T7 RNA polymerase system. This signal is about 30 nucleotides in length. Other 3' hairpins of shorter length can be used to provide good termination and RNA stability. Such hairpins can be inserted within the vector sequences to allow standard ribozymes to be placed in an appropriate orientation and expressed with such sequences attached.

Poly(A) tails are also useful to protect the 3' end of the ribozyme. These can be provided by either including a poly(A) signal site in the expression vector (to signal a cell to add the poly(A) tail in vivo), or by introducing a poly(A) sequence directly into the expression vector. In the first approach the signal must be located to prevent unwanted secondary structure formation with other parts of the ribozyme. In the second approach, the poly(A) stretch may reduce in size over time when expressed in vivo, and thus the vector may need to be checked over time. Care must be taken in addition of a poly(A) tail which binds poly(A) binding proteins which prevent the ribozyme from acting.

Ribozyme Testing

Once the desired ribozymes are selected, synthesized and purified, they are tested in kinetic and other experiments to determine their utility. An example of such a procedure is provided below.

Preparation of Ribozyme

Crude synthetic ribozyme (typically 350 µg at a time) was purified by separation on a 15% denaturing polyacrylamide gel (0.75 mm thick, 40 cm long) and visualized by UV shadowing. Once excised, gel slices containing full length ribozyme were soaked in 5 ml gel elution buffer (0.5M NH$_4$OAc, 1 mM EDTA) overnight with shaking at 4° C. The eluent was desalted over a C-18 matrix (Sep-Pak cartridges, Millipore, Milford, Mass.) and vacuum dried. The dried RNA was resuspended in 50–100 µl TE (TRIS 10 mM, EDTA 1 mM, DH 7.2). An aliquot of this solution was diluted 100 fold into 1 ml TE, half of which was used to spectrophotometrically quantitate the ribozyme solution. The concentration of this dilute stock was typically 150–800 nM. Purity of the ribozyme was confirmed by the presence of a single band on a denaturing polyacrylamide gel.

A ribozyme may advantageously be synthesized in two or more portions. (See Mamone, U.S. Ser. No. 07/882,689, filed May 11, 1992, hereby incorporated by reference herein.) Each portion of a ribozyme will generally have only limited or no enzymatic activity, and the activity will increase substantially (by at least 5–10 fold) when all portions are ligated (or otherwise juxtaposed) together. A specific example of hammerhead ribozyme synthesis is provided below.

The method involves synthesis of two (or more) shorter "half" ribozymes and ligation of them together using T4 RNA ligase. For example, to make a 34 mer ribozyme, two 17 mers are synthesized, one is phosphorylated, and both are gel purified. These purified 17 mers are then annealed to a DNA splint strand complementary to the two 17 mers. (Such a splint is not always necessary.) This DNA splint has a sequence designed to locate the two 17 mer portions with one end of each adjacent each other. The juxtaposed RNA molecules are then treated with T4 RNA ligase in the presence of ATP. The 34 mer RNA so formed is then HPLC purified.

Preparation of Substrates

Approximately 10–30 pmoles of unpurified substrate was radioactively 5' end-labelled with T4 polynucleotide kinase using 25 pmoles of [$\gamma$-$^{32}$p] ATP. The entire labelling mix was separated on a 20% denaturing polyacrylamide gel and visualized by autoradiography. The full length band was excised and soaked overnight at 4° C. in 100 µl of TE (10 mMTris-HCl pH 7.6, 0.1 mM EDTA).

Kinetic Reactions

For reactions using short substrates (between 8 and 16 bases) a substrate solution was made 1X in assay buffer (75 mM Tris-HCl, pH 7.6; 0.1 mM EDTA, 10 mM MgCl$_2$) such that the concentration of substrate was less than 1 nM. A ribozyme solution (typically 20 nM) was made 1X in assay buffer and four dilutions were made using 1X assay buffer. Fifteen µl of each ribozyme dilution (i.e., 20, 16, 12, 8 and 4 nM) was placed in a separate tube. These tubes and the substrate tube were pre-incubated at 37° C. for at least five minutes.

The reaction was started by mixing 15 µl of substrate into each ribozyme tube by rapid piperring (note that final ribozyme concentrations were 10, 8, 6, 4, 2 nM). 5 µl aliquots were removed at 15 or 30 second intervals and quenched with 5 µl stop solution (95% formamide, 20 mM EDTA xylene cyanol, and bromphenol blue dyes). Following the final ribozyme time point, an aliquot of the remaining substrate was removed as a zero ribozyme control.

The samples were separated on either 15% or 20% polyacrylamide gels. Each gel was visualized and quantitated with an Ambis beta scanner (Ambis Systems, San Diego, Calif.).

For the most active ribozymes, kinetic analyses were performed in substrate excess to determine $K_m$ and $K_{cat}$ values.

For kinetic reactions with long RNA substrates (greater than 15 bases in length) the substrates were prepared by transcription using T7 RNA polymerase and defined templates containing a T7 promoter, and DNA encoding appropriate nucleotides of the target RNA. The substrate solution is made 1X in assay buffer (75 mM Tris-HCl, pH 7.6; 0.1 mM EDTA; 10 mM MgCl$_2$) and contains 58 nanomolar concentration of the long RNA molecules. The reaction is started by addition of gel purified ribozymes to 1µM concentration. Aliquots are removed at 20, 40, 60, 80 and 100 minutes, then quenched by the addition of 5 µl stop solution. Cleavage products are separated using denaturing PAGE. The bands are visualized and quantitated with an Ambis beta scanner.

Kinetic Analysis

A simple reaction mechanism for ribozyme-mediated cleavage is:

$$R + S \underset{k_{-1}}{\overset{k_1}{\leftrightarrows}} [R{:}S] \overset{k_2}{\leftrightarrows} [R{:}P] \boxed{\rightarrow R + P}$$

where R=ribozyme, S=substrate, and P=products. The boxed step is important only in substrate excess. Because ribozyme concentration is in excess over substrate concentration, the concentration of the ribozyme-substrate complex ([R:S]) is constant over time except during the very brief time when the complex is being initially formed, i.e.,:

$$\frac{d[R{:}S]}{dt} = 0$$

where t=time, and thus:

$$(R)\,(S)k_1 = (RS)\,(k_2 + k_1).$$

The rate of the reaction is the rate of disappearance of substrate with time:

$$\text{Rate} = \frac{-d(S)}{dt} = k_2(RS)$$

Substituting these expressions:

$$(R)(S)k_1 = 1/k_2 \frac{-d(S)}{dt} (k_2 + k_1)$$

or:

$$\frac{-d(S)}{S} = \frac{k_1 k_2}{(k_2 + k_1)} (R)\,dt$$

Integrating this expression with respect to time yields:

$$-\ln \frac{S}{S_0} = \frac{k_1 k_2}{(k_2 + k_1)} (R)\,t$$

where $S_0$=initial substrate. Therefore, a plot of the negative log of fraction substrate uncut versus time (in minutes) yields a straight line with slope:

$$\text{slope} = \frac{k_1 k_2}{(k_2 + k_1)} (R) = k_{obs}$$

where $k_{obs}$=observed rate constant. A plot of slope ($k_{obs}$) versus ribozyme concentration yields a straight line with a slope which is:

$$\text{slope} = \frac{k_1 k_2}{(k_2 + k_1)} \text{ which is } \frac{k_{cat}}{K_m}$$

Using these equations the data obtained from the kinetic experiments provides the necessary information to determine which ribozyme tested is most useful, or active. Such ribozymes can be selected and tested in in vivo or ex vivo systems.

Liposome Preparation

Lipid molecules are dissolved in a volatile organic solvent ($CHCl_3$, methanol, diethylether, ethanol, etc.). The organic solvent is removed by evaporation. The lipid is hydrated into suspension with 0.1x phosphate buffered saline (PBS), then freeze-thawed 3x using liquid nitrogen and incubation at room temperature. The suspension is extruded sequentially through a 0.4 µm, 0.2 µm and 0.1 µm polycarbonate filters at maximum pressure of 800 psi. The ribozyme is mixed with the extruded liposome suspension and lyophilized to dryness. The lipid/ribozyme powder is rehydrated with water to one-tenth the original volume. The suspension is diluted to the minimum volume required for extrusion (0.4 ml for 1.5 ml barrel and 1.5 ml for 10 ml barrel) with 1×PBS and reextruded through 0.4 µm, 0.2 µm, 0.1 µm polycarbonate filters. The liposome entrapped ribozyme is separated from untrapped ribozyme by gel filtration chromatography (SEPHAROSE CL-4B, BIOGEL A5M). The liposome extractions are pooled and sterilized by filtration through a 0.2 µm filter. The free ribozyme is pooled and recovered by ethanol precipitation. The liposome concentration is determined by incorporation of a radioactive lipid. The ribozyme concentration is determined by labeling with $^{32}p$. Rossi et al., 1992 supra (and references cited therein) describe other methods suitable for preparation of liposomes.

In Vivo Assay

The efficacy of action of a chosen ribozyme may be tested in vivo by use of transformed cells containing the target mRNA using standard procedures.

Ribonuclease Protection Assay

The accumulation of target mRNA in cells or the cleavage of the RNA by ribozymes or RNAseH (in vitro or in vivo) can be quantified using an RNAse protection assay. (See McSwiggen, U.S. Ser. Nos. 07/883,849 and 07/884,073, both filed May 14, 1992, hereby incorporated by reference herein.)

In this method, antisense riboprobes are transcribed from template DNA using T7 RNA polymerase (U.S. Biochemicals) in 20 µl reactions containing 1X transcription buffer (supplied by the manufacturer), 0.2 mM ATP, GTP and UTP, 1 U/µl pancreatic RNAse inhibitor (Boehringer Mannheim Biochemicals) and 200 µCi $^{32}$p-labeled CTP (800 Ci/mmol, New England Nuclear) for 1 hour at 37° C. Template DNA is digested with 1 U RNAse-free DNAse I (U.S. Biochemicals, Cleveland, Ohio) at 37° C. for 15 minutes and unincorporated nucleotides removed by G-50 SEPHADEX spin chromatography.

In a manner similar to the transcription of antisense probe, the target RNA can be transcribed in vitro using a suitable DNA template. The transcript is purified by standard methods and digested with ribozyme at 37° C. according to methods described later.

Alternatively, cells are harvested into 1 ml of PBS, transferred to a 1.5 ml EPPENDORF tube, pelleted for 30 seconds at low speed in a microcentrifuge, and lysed in 70 µl of hybridization buffer (4M guanidine isothiocyanate, 0.1% sarcosyl, 25 mM sodium citrate, pH 7.5). Cell lysate (45 µl) or defined amounts of in vitro transcript (also in hybridization buffer) is then combined with 5 µl of hybridization buffer containing $5\times10^5$ cpm of each antisense riboprobe in 0.5 ml Eppendorf tubes, overlaid with 25 µl mineral oil, and hybridization accomplished by heating overnight at 55° C. The hybridization reactions are diluted into 0.5 ml RNAse solution (20 U/ml RNAse A, 2 U/ml RNAse T1, 10 U/ml RNAse-free DNAse I in 0.4M NaCl), heated for 30 minutes at 37° C., and 10 µl of 20% SDS and 10 µl of Proteinase K (10 mg/ml) added, followed by an additional 30 minutes incubation at 37° C. Hybrids are partially purified by extraction with 0.5 ml of a 1:1 mixture of phenol/chloroform; aqueous phases are combined with 0.5 ml isopropanol, and RNAse-resistant hybrids pelleted for 10 minutes at room temperature (about 20° C.) in a microcentrifuge. Pellets are dissolved in 10 µl loading buffer (95% formamide, 1X TBE, 0.1% bromophenol blue, 0.1% xylene cylanol), heated to 95° C. for five minutes, cooled on ice, and analyzed on 4%. polyacrylamide/7M urea gels under denaturing conditions.

Ribozyme Stability

The chosen ribozyme can be tested to determine its stability, and thus its potential utility. Such a test can also be used to determine the effect of various chemical modifications (e.g., addition of a poly(A) tail) on the ribozyme stability and thus aid selection of a more stable ribozyme. For example, a reaction mixture contains 1 to 5 pmoles of 5' (kinased) and/or 3' labeled ribozyme, 15 µg of cytosolic extract and 2.5 mM $MgCl_2$ in a total volume of 100 µl. The reaction is incubated at 37° C. Eight µl aliquots are taken at timed intervals and mixed with 8 µl of a stop mix (20 mM EDTA, 95% formamide). Samples are separated on a 15% acrylamide sequencing gel, exposed to film, and scanned with an Ambis.

A 3'-labelled ribozyme can be formed by incorporation of the $^{32}$P-labeled cordycepin at the 3' OH using poly(A) polymerase. For example, the poly(A) polymerase reaction contains 40 mM Tris, pH 8, 10 mM $MgCl_2$, 250 mM NaCl, 2.5 mM $MnCl_2$,; 3 µl $p^{32}$ cordycepin, 500 Ci/mM; and 6 units poly(A) polymerase in a total volume of 50 µl. The reaction mixture is incubated for 30 minutes at 37° C.

Effect of base substitution upon Ribozyme Activity

To determine which primary structural characteristics could change ribozyme cleavage of substrate, minor base changes can be made in the substrate cleavage region recognized by a specific ribozyme. For example, the substrate sequences can be changed at the central "C" nucleotide, changing the cleavage site from a GUC to a GUA motif. (See McSwiggen, U.S. Ser. No. 07/884,074, filed May 14, 1992, hereby incorporated by reference herein.) The $K_{cat}/K_m$ values for cleavage using each substrate are then analyzed to determine if such a change increases ribozyme cleavage rates. Similar experiments can be performed to address the effects of changing bases complementary to the ribozyme binding arms. Changes predicted to maintain strong binding to the complementary substrate are preferred. Minor changes in nucleotide content can alter ribozyme/substrate interactions in ways which are unpredictable based upon binding strength alone. Structures in the catalytic core region of the ribozyme recognize trivial changes in either substrate structure or the three dimensional structure of the ribozyme/substrate complex.

To begin optimizing ribozyme design, the cleavage rates of ribozymes containing varied arm lengths, but targeted to the same length of short RNA substrate can be tested. Minimal arm lengths are required and effective cleavage varies with ribozyme/substrate combinations.

The cleavage activity of selected ribozymes can be assessed using target mRNA substrates. The assays are performed in ribozyme excess and approximate $K_{cat}/K_{min}$ values obtained. Comparison of values obtained with short and long substrates indicates utility in vivo of a ribozyme.

Intracellular Stability of liposome-delivered ribozymes

To test the stability of a chosen ribozyme in vivo the following test is useful. Ribozymes are $^{32}$p-end labeled, entrapped in liposomes and delivered to target mRNA-containing cells for three hours. The cells are fractionated and ribozyme is purified by phenol/chloroform extraction. Alternatively, cells (1×10$^7$, T-175 flask) are scraped from the surface of the flask and washed twice with cold PBS. The cells are homogenized by douncing 35 times in 4 ml of TSE (10 mM Tris, pH 7.4, 0.25M Sucrose, mM EDTA). Nuclei are pelleted at 100xg for 10 minutes. Subcellular organelles (the membrane fraction) are pelleted at 200,000 xg for two hours using an SW60 rotor. The pellet is resuspended in 1 ml of H buffer (0.25M Sucrose, 50 mM HEPES, pH 7.4). The supernatant contains the cytoplasmic fraction (in approximately 3.7 ml). The nuclear pellet is resuspended in 1 ml of 65% sucrose in TM (50 mM Tris, pH 74., 2.5 mM MgCl$_2$) and banded on a sucrose step gradient (1 ml nuclei in 65% sucrose TM, 1 ml 60% sucrose TM, 1 ml 55% sucrose TM, 50% sucrose TM, 300 ul 25% sucrose TM) for one hour at 37,000xg with an SW60 rotor. The nuclear band is harvested and diluted to 10% sucrose with TM buffer. Nuclei are pelleted at 37,000xg using an SW60 rotor for 15 minutes and the pellet resuspended in 1 ml of TM buffer. Aliquots are size fractionated on denaturing polyacrylamide gels and the intracellular localization determined. By comparison to the migration rate of newly synthesized ribozyme, the various fraction containing intact ribozyme can be determined.

To investigate modifications which would lengthen the half-life of ribozyme molecules intracellularly, the cells may be fractioned as above and the purity of each fraction assessed by assaying enzyme activity known to exist in that fraction.

The various cell fractions are frozen at −70° C. and used to determine relative nuclease resistances of modified ribozyme molecules. Ribozyme molecules may be synthesized with 5 phosphorothioate (ps), or 2'Omethyl (2'-OMe) modifications at each end of the molecule. These molecules and a phosphodiester version of the ribozyme are end-labeled with $^{32}$p and ATP using T4 polynucleotide kinase. Equal concentrations are added to the cell cytoplasmic extracts and aliquots of each taken at 10 min. intervals. The samples are size fractionated by denaturing PAGE and relative rates of nuclease resistance analyzed by scanning the gel with an Ambis β-scanner. The results show whether the ribozymes are digested by the cytoplasmic extract, and which versions are relatively more nuclease resistant. Modified ribozymes generally maintain 80–90% of the catalytic activity of the native ribozyme when short RNA substrates are employed.

Unlabeled, 5' end-labeled or 3' end-labeled ribozymes can be used in the assays. These experiments can also be performed with human cell extracts to verify the observations.

Administration of Ribozyme

Selected ribozymes can be administered prophylactically, or to patients having colon carcinoma or pretumor cells, e.g., by exogenous delivery of the ribozyme to an infected tissue by means of an appropriate delivery vehicle, e.g., a liposome, a controlled release vehicle, by use of iontophoresis, electroporation or ion paired molecules, or covalently attached adducts, and other pharmacologically approved methods of delivery. Routes of administration include intramuscular, aerosol, oral (tablet or pill form), topical, systemic, ocular, intraperitoneal and/or intrathecal. Expression vectors for immunization with ribozymes and/or delivery of ribozymes are also suitable.

The specific delivery route of any selected ribozyme will depend on the use of the ribozyme. Generally, a specific delivery program for each ribozyme will focus on unmodified ribozyme uptake with regard to intracellular localization, followed by demonstration of efficacy. Alternatively, delivery to these same cells in an organ or tissue of an animal can be pursued. Uptake studies will include uptake assays to evaluate cellular ribozyme uptake, regardless of the delivery vehicle or strategy. Such assays will also determine the intracellular localization of the ribozyme following uptake, ultimately establishing the requirements for maintenance of steady-state concentrations within the cellular compartment containing the target sequence (nucleus and/or cytoplasm). Efficacy and cytotoxicity can then be tested. Toxicity will not only include cell viability but also cell function.

Some methods of delivery that may be used include:

a. encapsulation in liposomes, b. transduction by retroviral vectors, c. conjugation with cholesterol, d. localization to nuclear compartment utilizing nuclear targeting site found on most nuclear proteins, e. neutralization of charge of ribozyme by using nucleotide derivatives, and f. use of blood stem cells to distribute ribozymes throughout the body.

At least three types of delivery strategies are useful in the present invention, including: ribozyme modifications, particle carrier drug delivery vehicles, and retroviral expression vectors. Unmodified ribozymes, like most small molecules, are taken up by cells, albeit slowly. To enhance cellular uptake, the ribozyme may be modified essentially at random, in ways which reduce its charge but maintains specific functional groups. This results in a molecule which is able to diffuse across the cell membrane, thus removing the permeability barrier.

Modification of ribozymes to reduce charge is just one approach to enhance the cellular uptake of these larger molecules. The random approach, however, is not advisable since ribozymes are structurally and functionally more complex than small drug molecules. The structural requirements necessary to maintain ribozyme catalytic activity are well understood by those in the art. These requirements are taken into consideration when designing modifications to enhance cellular delivery. The modifications are also designed to reduce susceptibility to nuclease degradation. Both of these characteristics should greatly improve the efficacy of the ribozyme. Cellular uptake can be increased by several orders of magnitude without having to alter the phosphodiester linkages necessary for ribozyme cleavage activity.

Chemical modifications of the phosphate backbone will reduce the negative charge allowing free diffusion across the membrane. This principle has been successfully demonstrated for antisense DNA technology. The similarities in chemical composition between DNA and RNA make this a feasible approach. In the body, maintenance of an external concentration will be necessary to drive the diffusion of the modified ribozyme into the cells of the tissue. Administration routes which allow the diseased tissue to be exposed to a transient high concentration of the drug, which is slowly dissipated by systemic adsorption are preferred. Intravenous administration with a drug carrier designed to increase the circulation half-life of the ribozyme can be used. The size and composition of the drug carrier restricts rapid clearance from the blood stream. The carrier, made to accumulate at the site of infection, can protect the ribozyme from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity.

Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver RNA to cells and that the RNA remains biologically active.

For example, a liposome delivery vehicle originally designed as a research tool, Lipofectin, has been shown to deliver intact mRNA molecules to cells yielding production of the corresponding protein.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nonoparticles and hydrogels may be potential delivery vehicles for a ribozyme. These carriers have been developed for chemotherapeutic agents and protein-based pharmaceuticals, and consequently, can be adapted for ribozyme delivery.

Topical administration of ribozymes is advantageous since it allows localized concentration at the site of administration with slow, continuous systemic adsorption. This simplifies the delivery strategy of the ribozyme to the disease site and reduces the extent of toxicological characterization. Furthermore, the amount of material to be applied is far less than that required for other administration routes. Effective delivery requires the ribozyme to diffuse into the infected cells. Chemical modification of the ribozyme to neutralize negative charge may be all that is required for penetration. However, in the event that charge neutralization is insufficient, the modified ribozyme can be co-formulated with permeability enhancers, such as Azone or oleic acid, in a liposome. The liposomes can either represent a slow release presentation vehicle in which the modified ribozyme and permeability enhancer transfer from the liposome into the infected cell, or the liposome phospholipids can participate directly with the modified ribozyme and permeability enhancer in facilitating cellular delivery. In some cases, both the ribozyme and permeability enhancer can be formulated into a suppository formulation for slow release.

Ribozymes may also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the ribozyme to an accessible diseased tissue. Subcutaneous administration drains into a localized lymph node which proceeds through the lymphatic network into the circulation. The rate of entry into the circulation has been shown to be a function of molecular weight or size. The use of a liposome or other drug carrier localizes the ribozyme at the lymph node. The ribozyme can be modified to diffuse into the cell, or the liposome can directly participate in the delivery of either the unmodified or modified ribozyme to the cell.

A liposome formulation which can deliver oligonucleotides to lymphocytes and macrophages is also useful for certain cancerous conditions. This oligonucleotide delivery system prevents mRNA expression in affected primary immune cells. Whole blood studies show that the formulation is taken up by 90% of the lymphocytes after 8 hours at 37° C. Preliminary biodistribution and pharmacokinetic studies yielded 70% of the injected dose/gm of tissue in the spleen after one hour following intravenous administration.

Liposomes injected intravenously show accumulation in the liver, lung and spleen. The composition and size can be adjusted so that this accumulation represents 30% to 40% of the injected dose. The remaining dose circulates in the blood stream far up to 24 hours.

The chosen method of delivery should result in cytoplasmic accumulation and molecules should have some nuclease-resistance for optimal dosing. Nuclear delivery may be used but is less preferable. Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 100–200 mg/kg of body weight/day. The duration of treatment will extend through the course of the disease symptoms, possibly continuously. The number of doses will depend upon disease delivery vehicle and efficacy data from clinical trials.

Establishment of therapeutic levels of ribozyme within the cell is dependent upon the rate of uptake and degradation. Decreasing the degree of degradation will prolong the intracellular half-life of the ribozyme. Thus, chemically modified ribozymes, e.g., with modification of the phosphate backbone, or capping of the 5' and 3' ends of the ribozyme with nucleotide analogs may require different dosaging. Descriptions of useful systems are provided in the art cited above, all of which is hereby incorporated by reference herein.

The claimed ribozymes are also useful as diagnostic tools to specifically or non-specifically detect the presence of a target RNA in a sample. That is, the target RNA, if present in the sample, will be specifically cleaved by the ribozyme, and thus can be readily and specifically detected as smaller RNA species. The presence of such smaller RNA species is indicative of the presence of the target RNA in the sample.

Other embodiments are within the following claims.

We claim:

1. The enzymatic RNA molecule which specifically cleaves K-ras RNA.

2. The enzymatic RNA molecule of claim 1 wherein said enzymatic RNA molecule is in a hairpin, hepatitis delta virus, group I intron or RNase P RNA motif.

3. The enzymatic RNA molecule of claim 1 which specifically cleaves the sequence shown as any of SEQ. ID. NOS. 1–26, wherein said enzymatic RNA molecule is in the hepatitis delta virus motif.

4. The enzymatic RNA molecule of claim 1 wherein said enzymatic RNA molecule is in a hammerhead motif.

5. The enzymatic RNA molecule of claim 1, which specifically cleaves the sequence shown as any of SEQ. ID. NOS. 1,4–15,17–23, 25 or 26—26, wherein said enzymatic RNA molecule is in the hammerhead motif.

6. The enzymatic RNA molecule of claim 1 wherein said enzymatic RNA molecule comprises between 5 and 23 bases complementary to said RNA.

7. The enzymatic RNA molecule of claim 1 wherein said enzymatic RNA molecule comprises between 10 and 18 bases complementary to said RNA.

8. The enzymatic RNA molecule of any one of claims 1–7 wherein the enzymatic RNA molecule comprises an 2'-O-methyl modification in at least one sugar moiety.

9. The enzymatic RNA molecule of any one of claim 1–7 or wherein said enzymatic RNA molecule comprises at least one phosphorothioate group.

10. A mammalian cell comprised of an enzymatic RNA molecule of any one of claims 1–7.

11. The cell of claim 10, wherein the cell is a human cell.

12. A mammalian cell comprised of a nucleic acid encoding the enzymatic RNA molecule of any one of claims 1–7 in a manner which allows expression of the enzymatic RNA molecule within the mammalian cell.

* * * * *

UNITED STATES PATENT AND TRADEMARK OFFICE
CERTIFICATE OF CORRECTION

PATENT NO. : 5,610,052
DATED : March 11, 1997
INVENTOR(S) : James D. Thompson et al It is certified that error appears in the above-identified patent and that said Letters Patent is hereby corrected as shown below:

Column 9, Line 63: delete "piperring" and insert -- pipetting--.

Column 16 Line 53: delete "far" and insert --for--.

Signed and Sealed this

Seventh Day of April, 1998

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 26

( 2 ) INFORMATION FOR SEQ ID NO: 1:

( i ) SEQUENCE CHARACTERISTICS:
        ( A ) LENGTH: 12
        ( B ) TYPE: nucleic acid
        ( C ) STRANDEDNESS: single
        ( D ) TOPOLOGY: linear ( i i ) SEQUENCE DESCRIPTION: SEQ ID NO: 1:

UCCUAGGCGG CG                                                    1 2

( 2 ) INFORMATION FOR SEQ ID NO: 2:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) SEQUENCE DESCRIPTION: SEQ ID NO: 2:

GGCGGCGGAG GCAGCAGCG                                    1 9

( 2 ) INFORMATION FOR SEQ ID NO: 3:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i i ) SEQUENCE DESCRIPTION: SEQ ID NO: 3:

GGCAGUGGCG GCGG                                              1 4

( 2 ) INFORMATION FOR SEQ ID NO: 4:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) SEQUENCE DESCRIPTION: SEQ ID NO: 4:

CGGCUCGGCC AGUACUCCCG GCCC                        2 4

( 2 ) INFORMATION FOR SEQ ID NO: 5:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( i i ) SEQUENCE DESCRIPTION: SEQ ID NO: 5:

GCGCAGGCAC UGAAGGCGGC GGCGGGGCCA GAGGCUCAG          39

( 2 ) INFORMATION FOR SEQ ID NO: 6:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 6:

AUAAACUUGU GGUAGUUGGA GCUUGUGGCG U          31

( 2 ) INFORMATION FOR SEQ ID NO: 7:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i i ) SEQUENCE DESCRIPTION: SEQ ID NO: 7:

UGACGAUACA GCUA          14

( 2 ) INFORMATION FOR SEQ ID NO: 8:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 8:

UUGUGGACGA AUAUGAUCCA ACAAUA          26

( 2 ) INFORMATION FOR SEQ ID NO: 9:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO: 9:

UCCUACAGGA AGCAAGUAGU AAUUGAU          27

( 2 ) INFORMATION FOR SEQ ID NO: 10:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 10:

AAGAGGAGUA CAGUGCAAUG AGGGA          25

( 2 ) INFORMATION FOR SEQ ID NO: 11:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 11:

```
        AUUUGCCAUA  AAUAAUACUA  AAUCAUUUGA  A                    31
```

(2) INFORMATION FOR SEQ ID NO: 12:

(i) SEQUENCE CHARACTERISTICS:
        (A) LENGTH: 30
        (B) TYPE: nucleic acid
        (C) STRANDEDNESS: single
        (D) TOPOLOGY: linear (i i) SEQUENCE DESCRIPTION: SEQ ID NO: 12:

```
        GAUAUUCACC  AUUAUAGAGA  ACAAAUUAAA                       30
```

(2) INFORMATION FOR SEQ ID NO: 13:

(i) SEQUENCE CHARACTERISTICS:
        (A) LENGTH: 36
        (B) TYPE: nucleic acid
        (C) STRANDEDNESS: single
        (D) TOPOLOGY: linear (i i) SEQUENCE DESCRIPTION: SEQ ID NO: 13:

```
GAAGAUGUAC  CUAUGGUCCU  AGUAGGAAAU  AAAUGU                       36
```

(2) INFORMATION FOR SEQ ID NO: 14:

(i) SEQUENCE CHARACTERISTICS:
        (A) LENGTH: 22
        (B) TYPE: nucleic acid
        (C) STRANDEDNESS: single
        (D) TOPOLOGY: linear (i i) SEQUENCE DESCRIPTION: SEQ ID NO: 14:

```
        GAUUUGCCUU  CUAGAACAGU  AG                               22
```

(2) INFORMATION FOR SEQ ID NO: 15:

(i) SEQUENCE CHARACTERISTICS:
        (A) LENGTH: 11
        (B) TYPE: nucleic acid
        (C) STRANDEDNESS: single
        (D) TOPOLOGY: linear (i i) SEQUENCE DESCRIPTION: SEQ ID NO: 15:

```
        AUGGAAUUCC  U                                            11
```

(2) INFORMATION FOR SEQ ID NO: 16:

(i) SEQUENCE CHARACTERISTICS:
        (A) LENGTH: 14
        (B) TYPE: nucleic acid
        (C) STRANDEDNESS: single
        (D) TOPOLOGY: linear (i i) SEQUENCE DESCRIPTION: SEQ ID NO: 16:

```
        AAGACAAGAC  AGGG                                         14
```

(2) INFORMATION FOR SEQ ID NO: 17:

(i) SEQUENCE CHARACTERISTICS:
        (A) LENGTH: 11
        (B) TYPE: nucleic acid
        (C) STRANDEDNESS: single
        (D) TOPOLOGY: linear (i i) SEQUENCE DESCRIPTION: SEQ ID NO: 17:

```
        AGAAAUUCGA  A                                            11
```

( 2 ) INFORMATION FOR SEQ ID NO: 18:

( i ) SEQUENCE CHARACTERISTICS:
    ( A ) LENGTH: 36
    ( B ) TYPE: nucleic acid
    ( C ) STRANDEDNESS: single
    ( D ) TOPOLOGY: linear ( i i ) SEQUENCE DESCRIPTION: SEQ ID NO: 18:

AACAUAAAGA AAAGAUGAGC AAAGAUGGUA AAAAGA   36

( 2 ) INFORMATION FOR SEQ ID NO: 19:

( i ) SEQUENCE CHARACTERISTICS:
    ( A ) LENGTH: 29
    ( B ) TYPE: nucleic acid
    ( C ) STRANDEDNESS: single
    ( D ) TOPOLOGY: linear ( i i ) SEQUENCE DESCRIPTION: SEQ ID NO: 19:

AGAAAAGAA GUCAAAGACA AAGUGUGUA   29

( 2 ) INFORMATION FOR SEQ ID NO: 20:

( i ) SEQUENCE CHARACTERISTICS:
    ( A ) LENGTH: 14
    ( B ) TYPE: nucleic acid
    ( C ) STRANDEDNESS: single
    ( D ) TOPOLOGY: linear ( i i ) SEQUENCE DESCRIPTION: SEQ ID NO: 20:

UAAGGCAUAC UAGU   14

( 2 ) INFORMATION FOR SEQ ID NO: 21:

( i ) SEQUENCE CHARACTERISTICS:
    ( A ) LENGTH: 13
    ( B ) TYPE: nucleic acid
    ( C ) STRANDEDNESS: single
    ( D ) TOPOLOGY: linear ( i i ) SEQUENCE DESCRIPTION: SEQ ID NO: 21:

ACUAAAUUAU UAG   13

( 2 ) INFORMATION FOR SEQ ID NO: 22:

( i ) SEQUENCE CHARACTERISTICS:
    ( A ) LENGTH: 15
    ( B ) TYPE: nucleic acid
    ( C ) STRANDEDNESS: single
    ( D ) TOPOLOGY: linear ( i i ) SEQUENCE DESCRIPTION: SEQ ID NO: 22:

UUUAGCAUUA CCUAA   15

( 2 ) INFORMATION FOR SEQ ID NO: 23:

( i ) SEQUENCE CHARACTERISTICS:
    ( A ) LENGTH: 22
    ( B ) TYPE: nucleic acid
    ( C ) STRANDEDNESS: single
    ( D ) TOPOLOGY: linear ( i i ) SEQUENCE DESCRIPTION: SEQ ID NO: 23:

CUGCUCCAUG CAGACUGUUA GC   22

( 2 ) INFORMATION FOR SEQ ID NO: 24:

( i ) SEQUENCE CHARACTERISTICS:
( A ) LENGTH: 14
( B ) TYPE: nucleic acid
( C ) STRANDEDNESS: single
( D ) TOPOLOGY: linear ( i i ) SEQUENCE DESCRIPTION: SEQ ID NO: 24:

AAAAUGACAG UGGA                       14

( 2 ) INFORMATION FOR SEQ ID NO: 25:

( i ) SEQUENCE CHARACTERISTICS:
( A ) LENGTH: 13
( B ) TYPE: nucleic acid
( C ) STRANDEDNESS: single
( D ) TOPOLOGY: linear ( i i ) SEQUENCE DESCRIPTION: SEQ ID NO: 25:

UAUUCCAGA GUU                         13

( 2 ) INFORMATION FOR SEQ ID NO: 26:

( i ) SEQUENCE CHARACTERISTICS:
( A ) LENGTH: 15
( B ) TYPE: nucleic acid
( C ) STRANDEDNESS: single
( D ) TOPOLOGY: linear ( i i ) SEQUENCE DESCRIPTION: SEQ ID NO: 26:

ACUAGCAAUG CCUGU                      15